United States Patent
García Bermejo et al.

(10) Patent No.: US 10,907,156 B2
(45) Date of Patent: Feb. 2, 2021

(54) MIR-127 AGENTS FOR USE IN THE TREATMENT OF RENAL FIBROSIS

(71) Applicant: FUNDACIÓN PARA LA INVESTIGACIÓN BIOMÉDICA DEL HOSPITAL UNIVERSITARIO RAMÓN Y CAJAL, Madrid (ES)

(72) Inventors: Laura García Bermejo, Madrid (ES); Elisa Conde Moreno, Madrid (ES); Sara Gimenez Moyano, Madrid (ES); Laura Martín Gómez, Madrid (ES)

(73) Assignee: FUNDACIÓN PARA LA INVESTIGACIÓN BIOMÉDICA DEL HOSPITAL UNIV. RAMÓN Y CAJAL, Madrid (ES)

( * ) Notice: Subject to any disclaimer, the term of this patent is extended or adjusted under 35 U.S.C. 154(b) by 11 days.

(21) Appl. No.: 16/326,058

(22) PCT Filed: Aug. 9, 2017

(86) PCT No.: PCT/EP2017/070223
§ 371 (c)(1),
(2) Date: Feb. 15, 2019

(87) PCT Pub. No.: WO2018/033454
PCT Pub. Date: Feb. 22, 2018

(65) Prior Publication Data
US 2019/0177728 A1 Jun. 13, 2019

(30) Foreign Application Priority Data
Aug. 19, 2016 (EP) .................................... 16382399

(51) Int. Cl.
| | | |
|---|---|---|
| *C12N 15/113* | (2010.01) | |
| *A61K 31/713* | (2006.01) | |
| *A61K 9/00* | (2006.01) | |
| *A61K 9/127* | (2006.01) | |
| *A61K 35/761* | (2015.01) | |

(52) U.S. Cl.
CPC .......... *C12N 15/113* (2013.01); *A61K 9/0019* (2013.01); *A61K 9/127* (2013.01); *A61K 31/713* (2013.01); *A61K 35/761* (2013.01); *C12N 2310/141* (2013.01)

(58) Field of Classification Search
None
See application file for complete search history.

(56) References Cited

U.S. PATENT DOCUMENTS

| | | |
|---|---|---|
| 4,373,071 A | 2/1983 | Itakura |
| 4,401,796 A | 8/1983 | Itakura |
| 4,415,732 A | 11/1983 | Caruthers et al. |
| 4,458,066 A | 7/1984 | Caruthers et al. |
| 4,500,707 A | 2/1985 | Caruthers et al. |
| 4,668,777 A | 5/1987 | Caruthers et al. |
| 4,973,679 A | 11/1990 | Caruthers et al. |
| 5,047,524 A | 9/1991 | Andrus et al. |
| 5,132,418 A | 7/1992 | Caruthers et al. |
| 5,153,319 A | 10/1992 | Caruthers et al. |
| 5,262,530 A | 11/1993 | Andrus et al. |
| 5,700,642 A | 12/1997 | Monforte et al. |
| 5,885,613 A | 3/1999 | Holland et al. |
| 2008/0020058 A1* | 1/2008 | Chen ........................ A61P 5/14 424/502 |

FOREIGN PATENT DOCUMENTS

| | | |
|---|---|---|
| EP | 3 029 156 A2 | 6/2016 |
| WO | 2010/053572 A2 | 5/2010 |
| WO | 2012/170930 A1 | 12/2012 |

OTHER PUBLICATIONS

Aguado-Fraile et al. PLoS One 2012, 7(9): e44305.*
N Engl J Med 2014, vol. 371, pp. 58-66.*
Kriegel et al. Circulation 2012, vol. 126, A16740.*
Aguado-Fraile et al., "A Pilot Study Identifying a Set of MicroRNAs as Precise Diagnostic Biomarkers of Acute Kidney Injury," *PLOS One* 10(6):1-15, 2015.
Fierro-Fernández et al., "miR-9-5p suppresses pro-fibrogenic transformation of fibroblasts and prevents organ fibrosis by targeting NOX4 and TGFBR2," *EMBO Reports* 16(10):1358-1377, 2015.
Klibanov et al., "Amphipathic polyethyleneglycols effectively prolong the circulation time of liposomes," *FEBS Letters* 268(1):235-237, 1990.
Lasic, "Novel applications of liposomes," *TIBTECH* 16:307-321, 1998.
Liang et al., "MicroRNA: a new frontier in kidney and blood pressure research," *Am. J. Physiol. Renal Physiol.* 297:F553-F558, 2009.
Lorenzen et al., "MicroRNAs as mediators and therapeutic targets in chronic kidney disease," *Nature Reviews. Nephrology* 7:286-294, 2011.
U.S. Appl. No. 61/494,882, filed Jun. 8, 2011, entitled "Lyophilized Liposomal Formulations" (70 pages).
Yang et al., "Renoprotective approaches and strategies in acute kidney injury," *Pharmacology & Therapeutics* 163:58-73, 2016.

\* cited by examiner

*Primary Examiner* — Tracy Vivlemore
(74) *Attorney, Agent, or Firm* — Seed Intellectual Property (57) ABSTRACT

The present invention provides, among other things, methods and compositions for the effective prophylactical or therapeutical treatment of Chronic kidney disease (CKD), particularly for the prophylactical or therapeutical treatment of the tubulointerstitial fibrosis associated to CKD, more particularly for the prophylactical or therapeutical treatment of renal fibrosis.

9 Claims, 8 Drawing Sheets
Specification includes a Sequence Listing.

Fig. 3 miR127 could modulate TGFb induced EMT

Fig. 8 miR127 is associated to chronic damage in mice

SEQUENCE LISTING

<160> NUMBER OF SEQ ID NOS: 2

<210> SEQ ID NO 1
<211> LENGTH: 22
<212> TYPE: RNA
<213> ORGANISM: Artificial Sequence
<220> FEATURE:
<223> OTHER INFORMATION: miRNA mimic for miR-127-3p

<400> SEQUENCE: 1
ucggauccgu cugagcuugg cu                      22

<210> SEQ ID NO 2
<211> LENGTH: 22
<212> TYPE: RNA
<213> ORGANISM: Artificial Sequence
<220> FEATURE:

```
<223> OTHER INFORMATION: irVana miRNA inhibitor for miR-127-3p

<400> SEQUENCE: 2
agccaagcuc agacggaucc ga                                              22
```

MIR-127 AGENTS FOR USE IN THE TREATMENT OF RENAL FIBROSIS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 370083_401USPC_SEQUENCE_LISTING. The text file is 820 bytes was created on Feb. 14, 2019, and is being submitted electronically via EFS-Web.

FIELD OF THE INVENTION

The present invention discloses a method of prophylactically or therapeutically treating Chronic kidney disease (CKD) or of reducing the risk of CKD disease progression in a patient comprising expressing miR-127 in the renal cells of said patient and suitable means for said methods.

BACKGROUND OF THE INVENTION

Chronic kidney disease (CKD) is a major public health problem that is closely linked to common diseases such as diabetes mellitus, hypertension or metabolic syndrome. Besides CKD may have other causes such as polycystic kidney disease (PKD), IgA nephropathy (IgAN), lupus nephritis, herbs and environmental toxins. CKD could also derive from previous episodes of Acute Renal Failure (ARF) or hypertension. Statistics in developed countries around the world indicate that CKD affects 11% of the population and this percentage is increasing due to the aging of the population and the increase in some of its etiologies such as diabetes mellitus. In addition, patients with CKD have a high risk of mortality, cardiovascular complications, bone loss and frequent fractures, loss of cognitive ability, among other complications. In the current treatment of CKD many therapies target the renin-angiotensin system, but they are not effective in the progression arrest of kidney disease and in later stages, patients required renal replacement therapy, dialysis or transplantation. Both renal replacement therapy and treatment of complications of CKD, represent a high economic cost to health services.

Regardless of etiology, the CKD is characterized by tubulointerstitial fibrosis, tubular atrophy and glomerular sclerosis, as a result of the excessive deposition of extracellular matrix (ECM), infiltration of inflammatory cells, hypertrophy of mesangial cells and apoptosis of podocytes. In particular, there are several key cellular processes that contribute to the appearance of Chronic kidney disease (CKD):
  i) the proliferation and transformation of resident fibroblasts to myofibroblasts, which secrete abnormal extracellular matrix proteins such as collagen I, which is deposited and contribute crucially to fibrosis;
  ii) the proximal tubular epithelial cells undergo a process of epithelial-mesenchymal transition (EMT) which contributes to their dysfunction and fibrosis;
  iii) vascular pericytes undergo transition to mesenchymal cells and myofibroblasts;
  iv) homeostasis loss of endothelial cells entering apoptosis resulting in vascular rarefaction.
  v) Inflammatory infiltration, in particular of monocyte-macrophages, and resident macrophages exchanging M1 and M2 phenotype during progression of the disease. Indeed, mouse models have demonstrated the appearance of macrophages M2 associated with the progression of chronic damage.

All of these cellular processes contribute to the progression of renal fibrosis (tubulointerstitial fibrosis), and organ dysfunction and thus to the appearance of CKD. In all these cellular processes, β1 transforming growth factor (TGF-β1) plays a key role as a promoter of tubulointerstitial fibrosis. The synthesis of TGF-β1 by resident renal cells and infiltrating inflammatory cells may occur in response to various stimuli including high glucose, Angiotensin II or reactive oxygen species. This factor is associated with pathological events in the tubulointerstitial compartment (EMT and fibroblast proliferation), the glomerular compartment (hypertrophy and apoptosis) and vascular compartment (endothelial-mesenchymal transition, EndMT). These effects are mediated by the binding of TGF-β to its type 2 receptors (TGF-BR2) that recruits and activates receptors TGF-β type 1 (TGFBR1), starting intracellular signaling Smad proteins dependent pathways, although other routes not dependent on Smad proteins including pp60c-src, MAPK, p53 and PI3K/AKT may also be involved.

Recently it has been described that miRNAs are key regulators of the dependent TGF-β signaling. Most members of the TGF-β and its signaling pathways family are regulated by miRNAs, suggesting an auto-regulatory loop feedback between TGF-β and miRNAs in the generation of renal fibrosis. Therefore, miRNAs have emerged in recent years as regulatory mechanisms underlying renal fibrosis in CKD.

Since it has been shown that miRNAs and their deregulation mechanisms may be responsible for the development of some diseases, including renal fibrosis, they have been considered as new therapeutic targets. In this sense, to date a number of miRNAs associated with solid organ fibrosis, with pro-fibrotic and anti-fibrotic activity, have been described, such as miR-21, miR-29, miR-192 and the miR-200 family. However, to date there is still a need to provide a method of prophylactically or therapeutically treating CKD, in particular of prophylactically or therapeutically treating the tubulointerstitial fibrosis associated to CKD.

BRIEF DESCRIPTION OF THE FIGURES

FIG. 1 shows MiRNAs expression in a TGF-β induced model. miRNAs were determined in proximal tubule epithelial cells HK2 treated with TGF-β added to the culture medium in different concentrations (1, 2.5 and 5 ng) during 48 h. Treated cells were harvested and RNA was extracted by trizol and phenol/chloroform extraction. After RNA quantification and purity estimation by Nanodrop, equal amounts of RNA in each condition were used for qRT-PCR. The amplification reaction was performed using specific LNA primers for each miRNA and SYBRGreen as fluorophore. As housekkeping control, RNU6B was amplified. Results are shown as fold change in comparison to non treated cells, using 2DDCT method for quantification. As it can be observed, miR127 is induced by TGF-β treatment in these cells.

FIG. 2. miR-127 was modulated in HK2 cells by cell transfection of pre-miR-127 (0.1 nM) and anti-miR-127 (100 nM) using lipofectamine 2000. After a 48 hrs transfection, HK2 cells were treated with TGF-☐ (5 and 10 ng) during 24 hrs. After TGF-β treatment, cells were harvested and the expression of genes associated to EMT such as e-cadherin, a-SMA, collagen I and fibronectin was determined by qRT-PCR. For this analysis, RNA was extracted by trizol and phenol/chloroform extraction. After RNA quantification and purity estimation by Nanodrop, equal amounts of RNA in each condition were used for qRT-PCR. The amplification reaction was performed using specific primers for each gene and SYBRGreen as as fluorophore. As housekeeping control, 28S gene was amplified. Results are shown as fold change in comparison to non treated cells, using 2DDCT method for quantification. As it can be observed, the inhibition of miR127 in TGFb treated cells promotes the reduction of e-cadherin expression, as epithelial marker, and the induction of α-SMA, collagen I and fibronectin I, as mesenchymal markers. The overexpression of miR127 in TGF-β treated cells reverts these effects, maintaining e-cadherin expression as epithelial marker. FIG. 3. miR-127 was modulated in HK2 cells by cell transfection of pre-miR-127 (0.1 nM) and anti-miR-127 (100 nM) using lipofectamine 2000. After a 48 hrs transfection, HK2 cells were treated with TGF-β (5 and 10 ng) during 24 h. After TGF-β treatment, cell morphology and α-SMA expression was determined by immunofluorescence, using specific anti-αSMA expression and fluorescence microcopy. As it can be observed, overexpression of miR-127 results in lower expression of α-SMA (lower green staining) and more importantly, results in the maintenance of epithelial monolayer and square cell morphology. The inhibition of miR127 results in flatter and elongated cell morphology, loss of monolayer formation and increased α-SMA expression. Altogether these results demonstrate that miR127 can modulate EMT in HK2 cells treated with TGFb as profibrotic agent, since overexpression of miR127 in HK2 cells maintain epithelial phenotype and miR127 inhibition promote mesenchymal phenotype in HK2 cells.

FIG. 4 shows that miR-127 can modulate TGF-b induced migration and MMPs activity. Upper part: Migration capacity of HK2 cells where miR-127 was modulated and treated with TGF-β was determined by wound healing assays. miR-127 was modulated in HK2 cells by cell transfection of pre-miR-127 (0.1 nM) and anti-miR-127 (100 nM) using lipofectamine 2000. After 48 h of transfection, HK2 cells were treated with TGF-β (5 and 10 ng) during 48 h. After 24 h of treatment, a healing in the monolayer is made using a pipet tip. Healing of the wound is monitorized during 24 h using a contrast phase microscope. As it can be observed, cells where miR-127 was inhibited by anti-miR-127 have migrated, trying to close the wound, whereas cells with miR-127 overexpression by pre-miR-127 did not migrate and wound stayed open in the monolayer. Lower part: Methaloproteinases (MMPs) activity in supernatants from HK2 transfected with pre-miR-127 and anti-miR-127 was determined by zymograme assays. These assays included the treatment of supernants with trypsin (1%) for MMP activation and the electrophoretic separation of MMPs in a matrix of polyacrylamide containing 2% of gelatin (general substrate for MMPs) and/or 2% of collagen I (substrate for MMP2 and MMP9). After electrophorectic resolution of MMPs by molecular weight, the gel was stained with bromophenol blue. In supernatants where MMPs were active, the gel matrix is digested and no staining is detected. The gel was observed by visible capturing equipment and inverse image was provided. As it can be observed slightly but consistent higher MMP activity was detected in supernatants from HK2 cells where miR-127 was inhibited by anti-miR-127, correlating with EMT and migration capacity in HK2 after miR127 inhibition. Altogether these results confirm that miR127 control EMT in HK2 cells treated with TGFb as profibrotic agent, since overexpression of miR127 reduced migratory capacity of HK2 cells by modulating MMPs activity, among other characteristics FIG. 5 shows that miR-127 is a mediator of macrophage polarization. Primary human macrophages were polarized in vitro by stimulation with different cytokines: GM-CSF+LPS to M1 phenotype; MCSF+IL4 to M2 phenotype and MCSF+IL-10 or TGF-β The polarization was observed by morphological alterations: M1 phenotype maintained a round cell morphology whereas M2 phenotype exhibited flatter and elongated cell morphology. Although there are not specific and accurate makers of polarized macrophages, CD163 expression is link to M2 macrophages. Thus, we polarized macrophages by treatments in vitro and confirmed by flow cytometry and specific CD163 markers that M2 macrophages expressed higher levels of CD163. Additionally and related to this, M2 macrophages expressed lower levels of miR-127 than M1 macrophages as indicated in the figure. In addition, it is noted that miR127 levels were determined by qRT-PCR using specific LNA primers for miR127 and SYBRGreen, in polarized macrophages. Furthermore, we were able to modulate miR-127 in macrophages by cell transfection of pre-miR-127 (15 nM) and antimiR-127 (50 nM) using lipofectamine 2000. In this sense, we efficiently overexpressed miR127 and inhibited miR127. miR127 levels were determined by qRT-PCR using specific LNA primers for miR-127 and SYBRGreen (right side of the figure). In macrophages overexpressing miR-127, arginine 1 as a M1 marker was induced and in macrophages where miR-127 was inhibited, arginine 2 as a M2 marker was higher. Results are shown as fold change in comparison to scrambled transfected cells (pre-miR srambled or negative, anti-miR scrambled or negative) using 2DDCT method for quantification. All of these results demonstrate that miR-127 is modulated in macrophages polarization and the exogenous modulation of miR-127 drives to macrophages polarization: mir127 overexpression to M1 phenotype and miR127 inhibition to M2 phenotype.

FIG. 6 shows that miR-127 modulates macrophage polarization in fibrotic microenvironment. Primary human macrophages cultured in supernatants from proximal epithelial cells HK2 where miR127 was modulated are also affected. In particular, macrophages cultured in supernatants from HK2 cells overexpressing miR-127 expressed higher levels of miR-127 and lower levels of Arginase 2, indicating that macrophages cultured in supernatants from HK2 cells overexpressing miR-127, polarized to M1 phenotype and macrophages cultured in supernatants from HK2 cells where miR-127 was inhibited, polarized to the M2 phenotype expressing higher levels of arginase 2. miR-127 and arginase 2 expression in macrophages cultures in supernatants from HK2 were determined by qRT-PCR with specific primers for miR127 and arginase 2 and SYBRGreen. Results are shown as fold change in comparison to scrambled transfected cells, using 2DDCT method for quantification. These results indicate that the supernatants from HK2 cells where miR-127 is modulated contains soluble factors relevant for the polarization of macrophages. Therefore, we performed a cytokine array in those supernatants. Such assay is an array of specific antibodies for each cytokine coupled to an ELISA method for detection. At the end, absorbance to 560 nm was used as direct quantification of the cytokines present in the supernatants. Raw data of absorbance are shown on the right-side of the figure. These results together demonstrate that miR127 can control the macrophages phenotype when modulated in macrophages but also miR127 modulated in fibrotic microenvironment including epithelial cells can affect macrophages polarization.

FIG. 7 shows that miR-127 can modulate fibrotic microenvironment by cytokines. We have performed a cytokine array. Such assay is an array of specific antibodies for each cytokine coupled to a ELISA method for detection. At the end, absorbance to 560 nm was used as direct quantification of the cytokines present in the supernatants. We analysed the quantification of absorbance by the supernatants from HK2 cells which have induced M1 or M2 phenotypes and representation of the cytokine levels in pg/ml is shown. As it can be observed, the supernatant that polarized to M1 phenotypes contained pro-inflammatory cytokines as expected and the supernatants that polarized to M2 phenotypes contained anti-inflammatory cytokines. These results together indicate that miR127 can also affects the polarization of the macrophages when this miRNA is modulated in the fibrotic microenvironment cells trough modulating the secretion of cytokines and other polarization factors FIG. 8 shows that miR-127 is associated to chronic damage in mice. We have set up a murine model of chronic damage by unilateral ureteral obstruction (UUO). In this model, after 5 days of evolution we can observe alterations in the renal tissue: proximal tubule distalization, fibroblasts accumulation in renal parenchyma and glomerular hypertrophy, by hematoxylin and eosin staining, in the UUO kidney in comparison to contralateral. In Masson staining, we can have observed collagen I deposition in renal parenchyma (Green-Blue staining) and also M2 macrophages presence by immunohistochemistry for YMC1, specific marker of M2 macrophages. In situ hybridization of miR-127 in renal tissue from mice at 5 days, indicate higher blue staining in UUO kidney in comparison to contralateral, confirming miR127 induction in damaged kidney. In situ hybridization includes the use of double DIG labeled specific probe for miR-127. All the renal tissue analysis have been performed in paraffine-embedded sections. Moreover by qRT-PCR in frozen renal tissue from mice, UUO and contralateral, after RNA extraction with trizol, we determined the expression levels of miR127 and as it can be observed, higher levels of miR127 in UUO in comparison to contralateral kidney are detected. As housekeeping control, RNU6B was amplified. Results are shown as fold change in comparison to contralateral cells, using 2DDCT method for quantification. All together these results demonstrated that miR127 is expressed in a fibrotic kidney of a murine model, which reproduce CKD in humans. Moreover, miR127 expression is associated to the renal damage.

DESCRIPTION OF THE INVENTION

Figure 1:
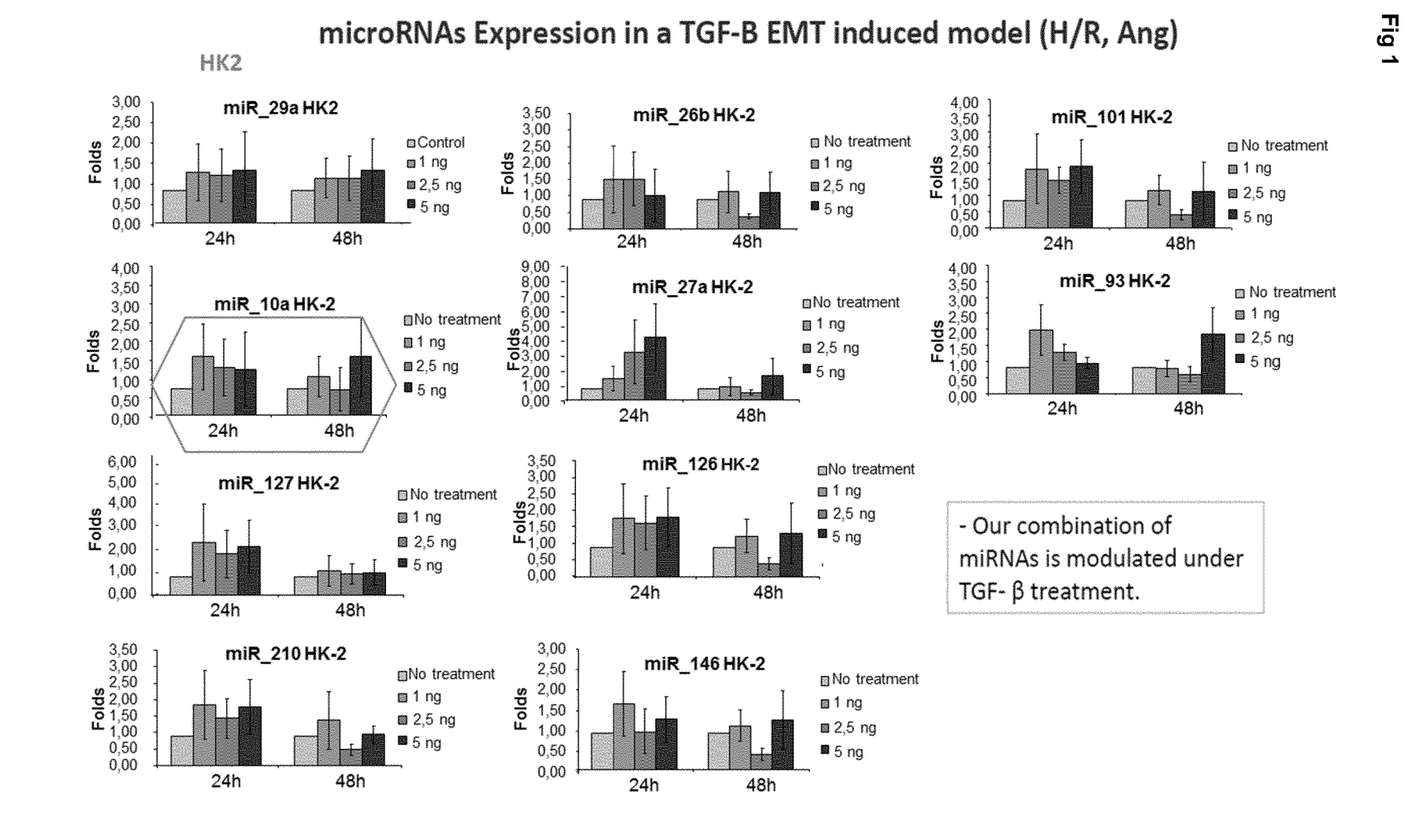
Figure 2:
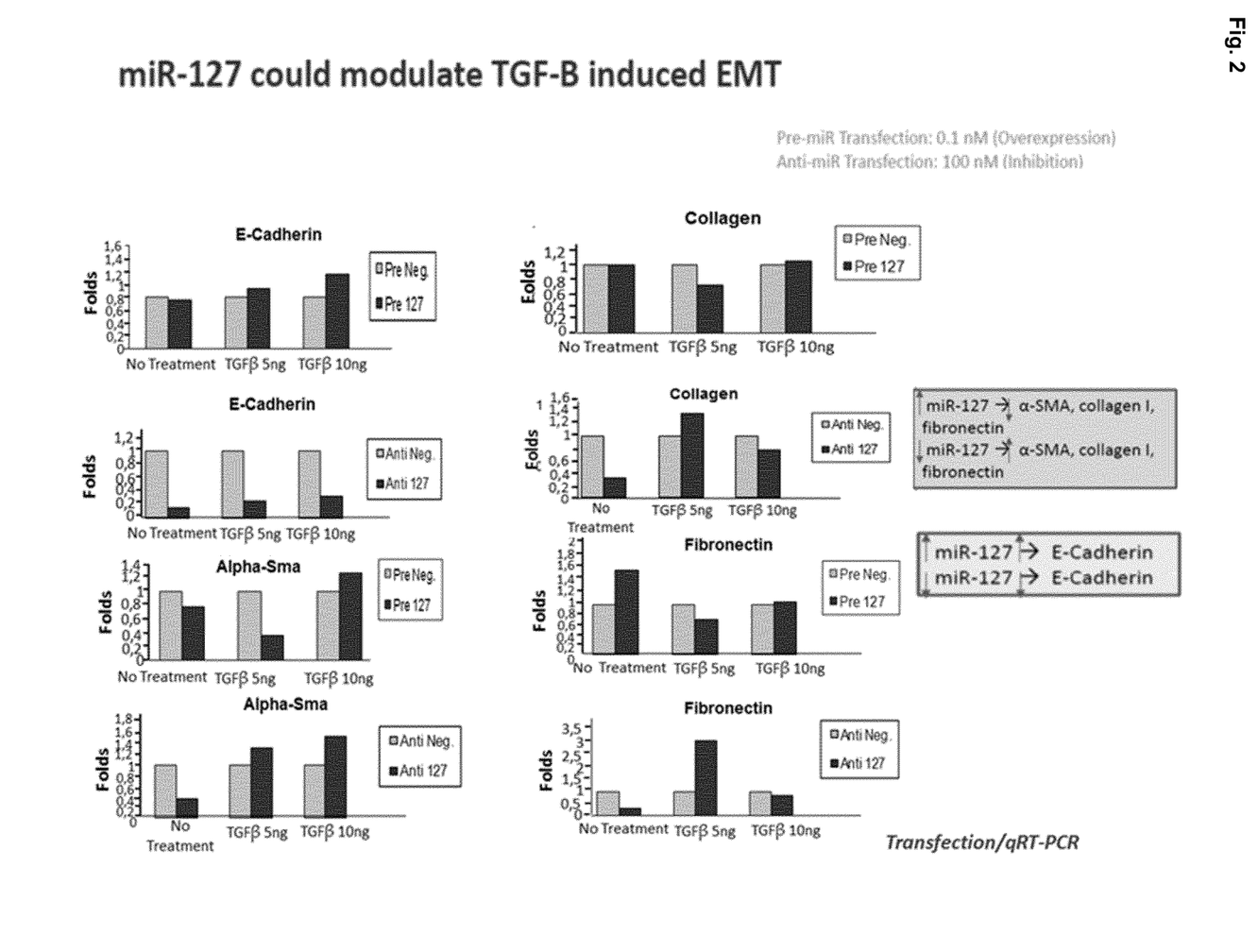
FIGS. 2 and 3 show that miR-127 can modulate TGF-β induced EMT.
Figure 3:
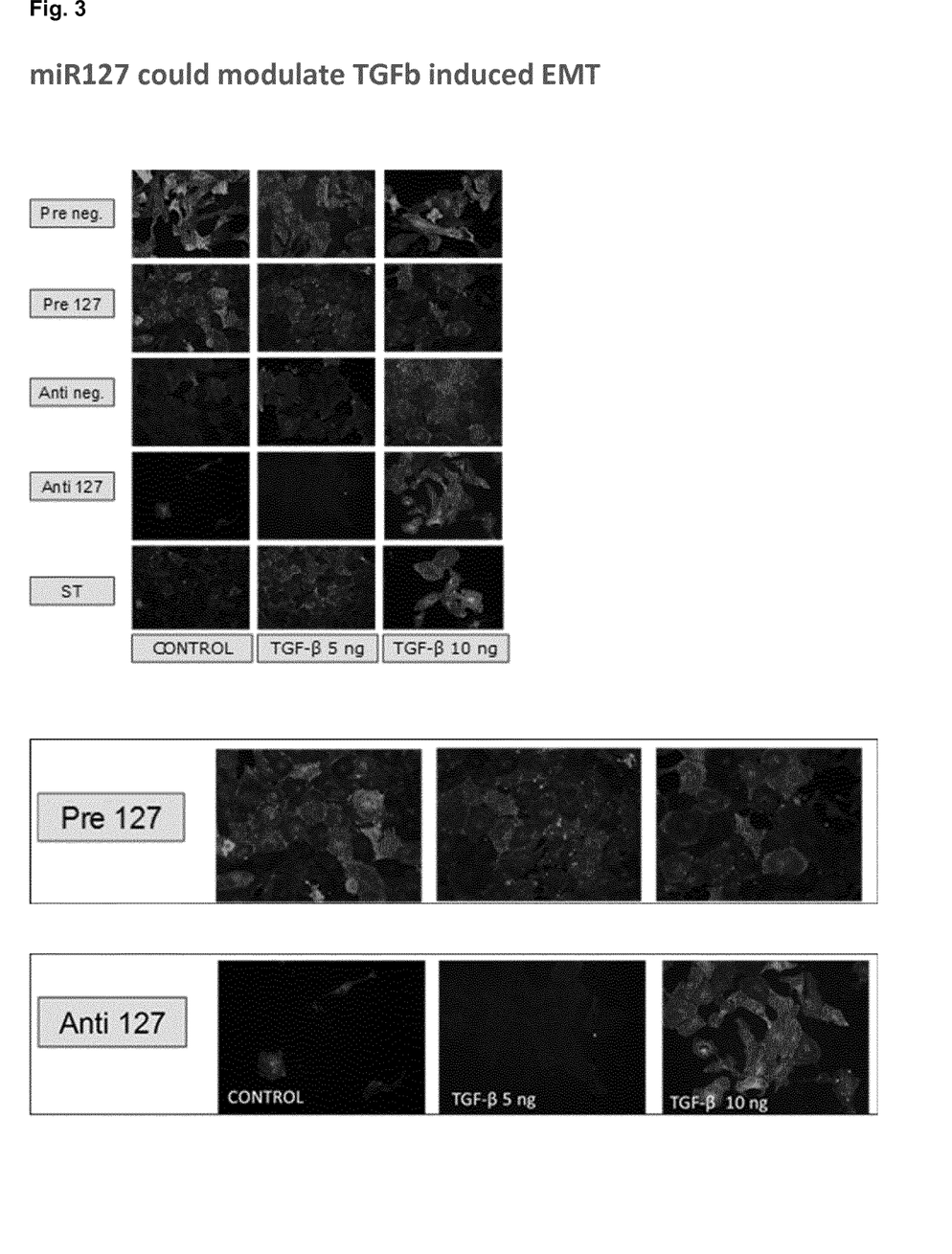
Figure 4:
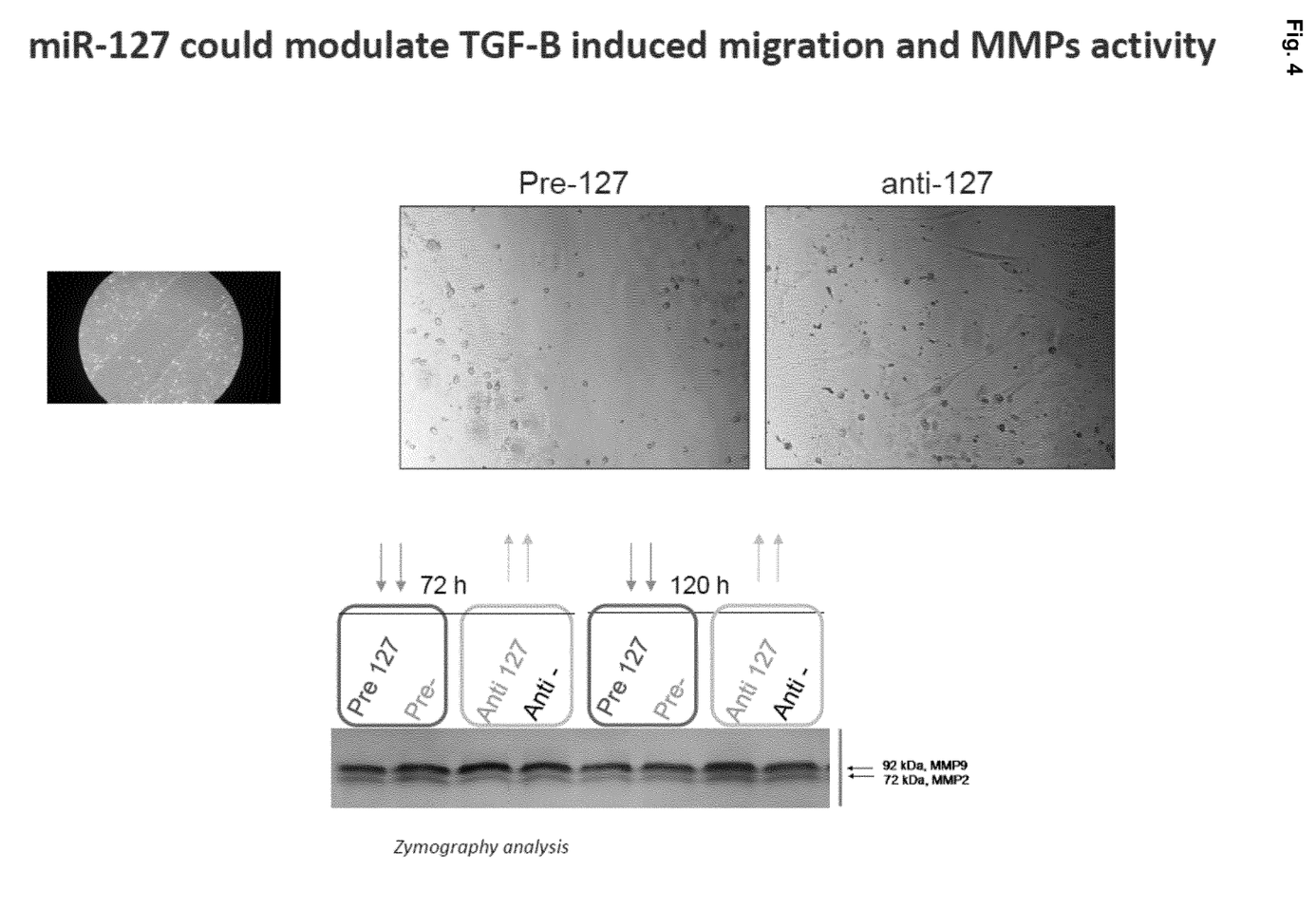
Figure 5:
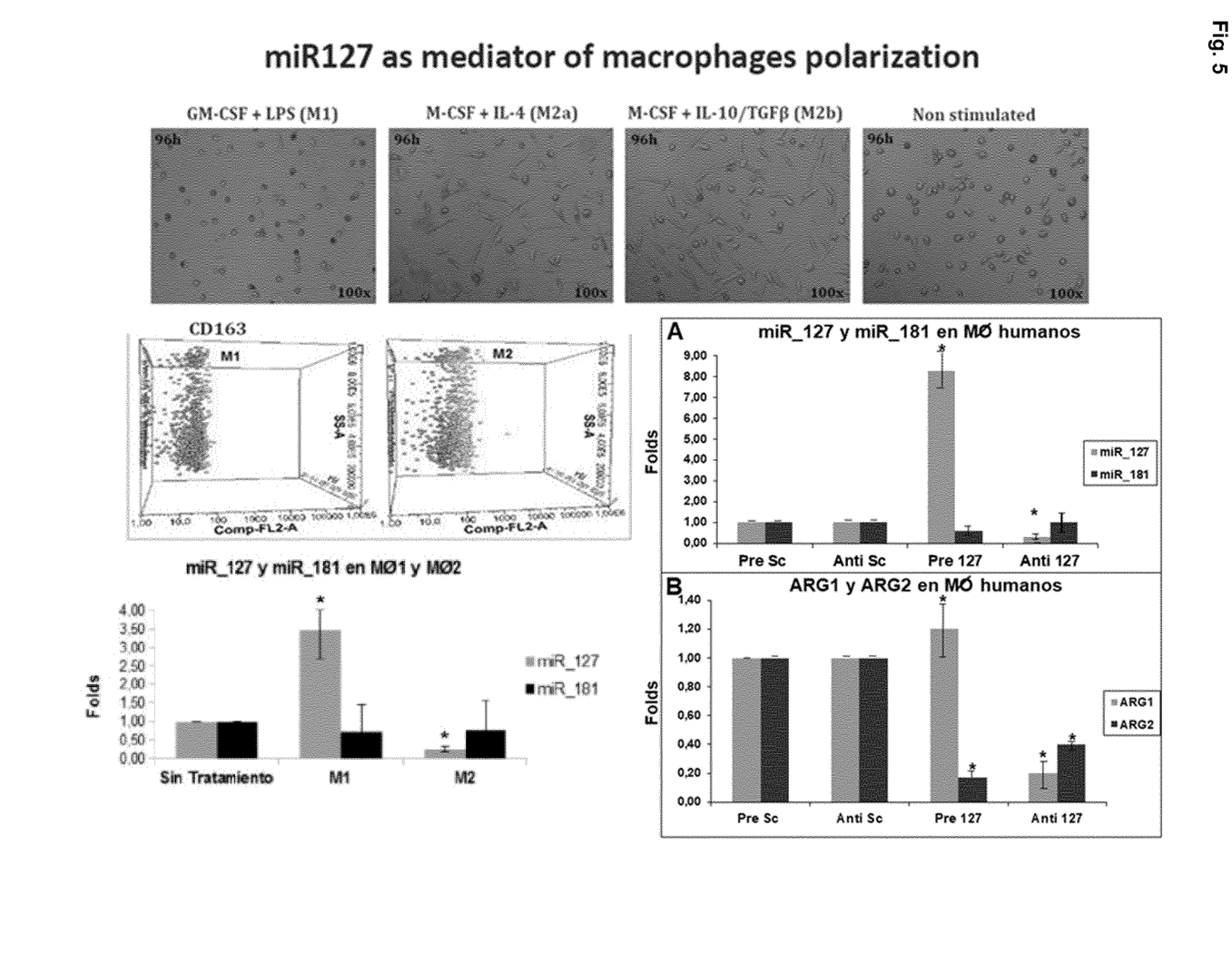
Figure 6:
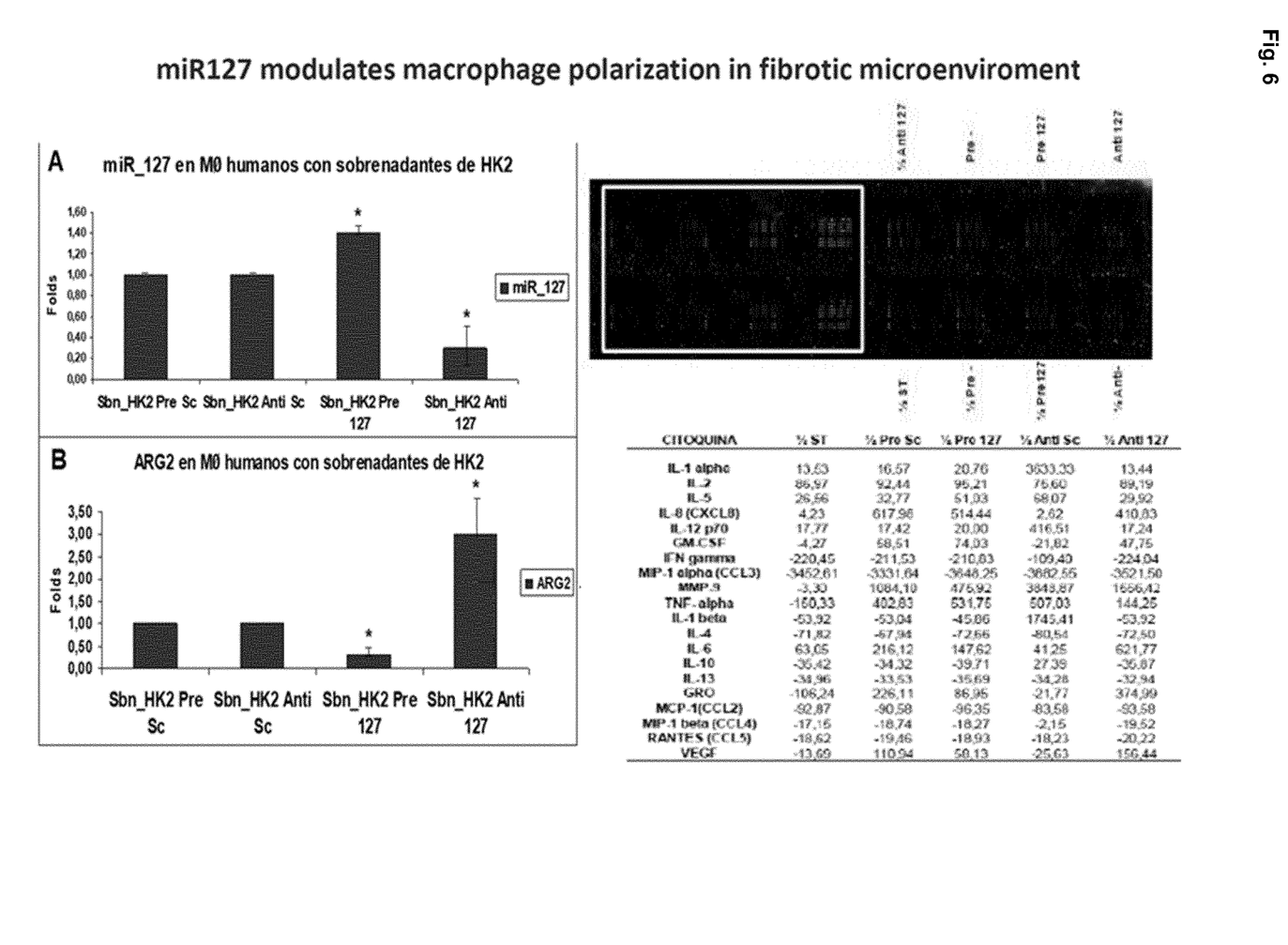
Figure 7:
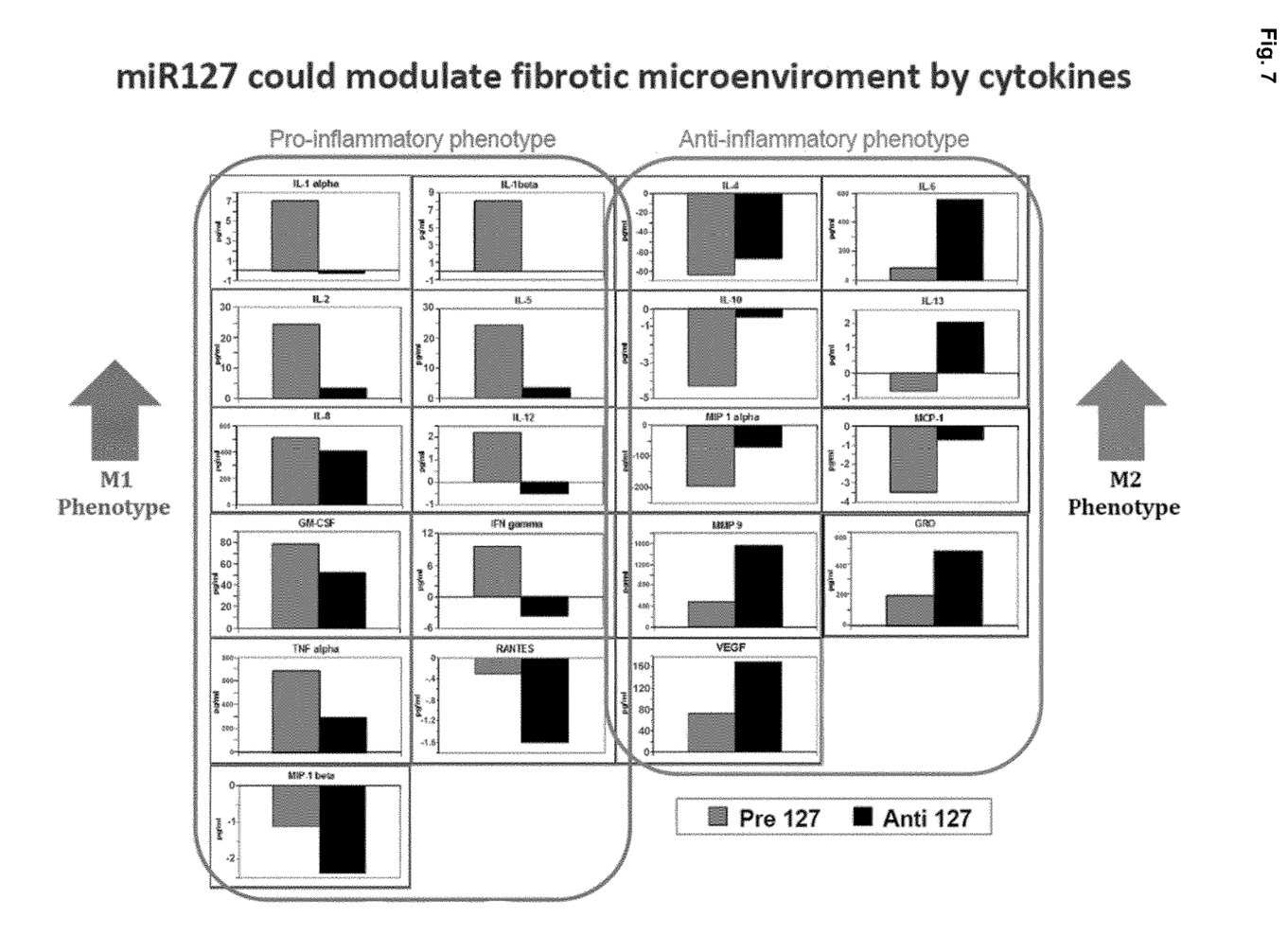
Figure 8:
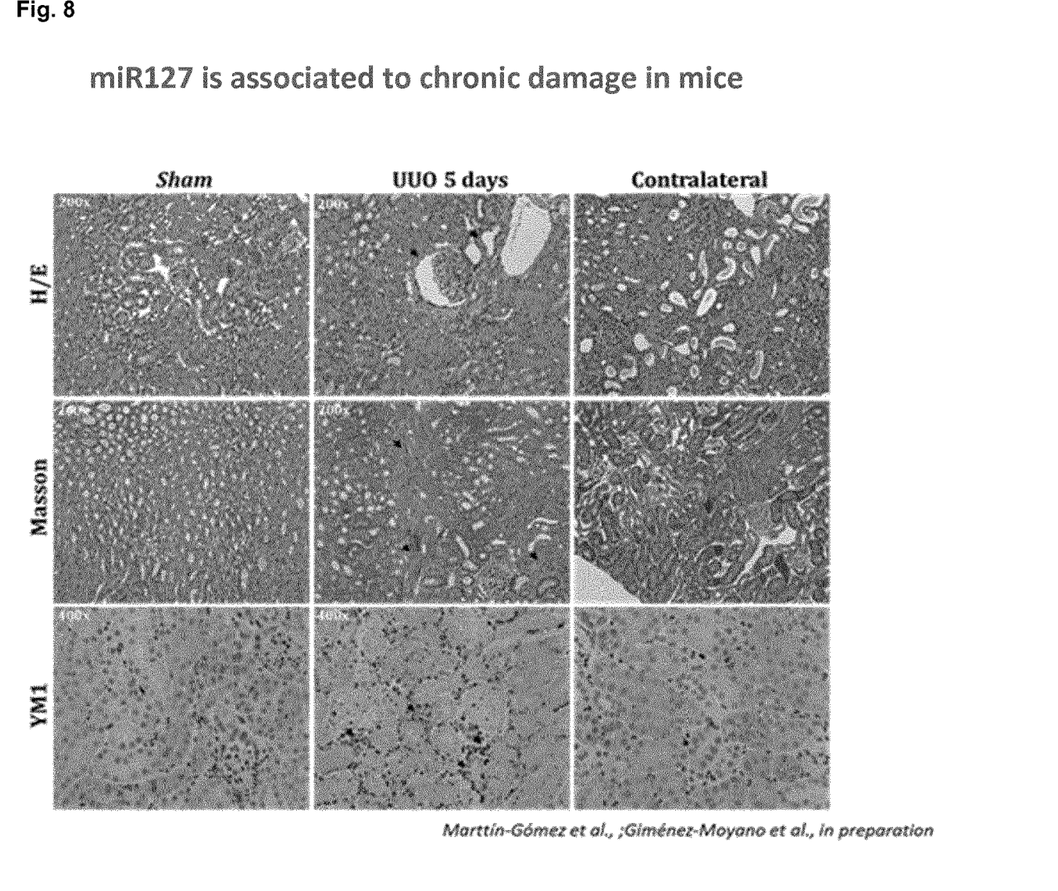

We have identified miR-127 (miR-127-3p) as an important regulator of chronic renal damage development and thus of the development of chronic kidney disease (CKD). In this sense, the results provided in the figures and the examples, indicate that in cultured human proximal tubular cells (HK2) treated with TGF-β (2.5, 5 and 10 ng/ml), or treated with Angiotensin (10 ng/ml), mimicking EMT induction leading to fibrosis, or subjected to long-term hypoxia/re-oxygenation protocol, mimicking evolution of acute ischemic injury towards chronic damage; the over expression of miR127, by transfection of specific pre-miR127, helps maintaining an epithelial phenotype and thus reducing tubulointerstitial fibrosis or renal fibrosis. This is indicated by the morphology and integrity of the monolayer of the tubular cells, the correct distribution of molecules in adherent junctions (ZO-1) and by the maintenance of the expression of molecules associated to epithelial phenotype (e-cadherin).

In contrast, inhibition of miR-127 promotes morphological changes, loss of monolayer integrity, expression of molecules associated to the mesenchymal phenotype (fibronectin, collagen I, α-SMA) and loss of epithelial phenotype as well as an increased activity of metalloproteinase (MMP2 and MMP9), all of these factors are key cellular processes that contribute to the appearance of tubulointerstitial fibrosis and thus to the appearance of Chronic kidney disease (CKD). In addition, in the wound-healing in vitro assays shown herein by using HK-2 cells, it is shown that overexpression of miR127 and stimulation with TGF-β of HK-2 cells inhibits cell migration during the wound healing process, in contrast, HK-2 cells where miR127 has been inhibited migrate upon TGF-β stimulation.

In light of these results, the present invention thus provides, among other things, methods and compositions for the effective prophylactical or therapeutical treatment of CKD, particularly for the prophylactical or therapeutical treatment of the tubulointerstitial fibrosis associated to CKD, more particularly for the prophylactical or therapeutical treatment of renal fibrosis. In is noted that for "therapeutical treatment" of a disease it is understood the treatment of a disease after the clinical manifestation of the same.

Thus in a first aspect of the present invention, the invention provides methods for the effective prophylactical or therapeutical treatment of CKD including administering in the kidney, particularly into the resident renal cells, of a subject in need of treatment a composition comprising a miR-127, a plasmid or vector comprising a sequence coding for miR-127, a precursor of miR127 or a plasmid or vector comprising a sequence coding for a precursor of miR-127 (pre-miR-127), or a miR-127 modulator capable of increasing the intracellular concentration of miR-127, at an effective dose and an administration interval such that at least one symptom or feature of CKD is reduced in intensity, severity, or frequency or has delayed in onset.

In a preferred embodiment of the first aspect of the invention, the resident renal cells are selected from the list consisting of Proximal tubular epithelial cells, fibroblast's renal cells and macrophages present in the kidneys. In another preferred embodiment, the resident renal cells are Proximal tubular epithelial cells and the composition comprises a miR-127, a plasmid or vector comprising a sequence coding for miR-127, a precursor of miR127 or a plasmid or vector comprising a sequence coding for a precursor of miR-127 (pre-miR-127), or a miR-127 modulator capable of increasing the intracellular concentration of miR-127. In another preferred embodiment, the resident renal cells are fibroblast's renal cells and composition comprises a miR-127, a plasmid or vector comprising a sequence coding for miR-127, a precursor of miR127 or a plasmid or vector comprising a sequence coding for a precursor of miR-127 (pre-miR-127), or a miR-127 modulator capable of increasing the intracellular concentration of miR-127. In another preferred embodiment, the resident renal cells are macrophages present in the kidneys and the composition comprises a miR-127, a plasmid or vector comprising a sequence coding for miR-127, a precursor of miR127 or a plasmid or vector comprising a sequence coding for a precursor of miR-127 (pre-miR-127), or a miR-127 modulator capable of increasing the intracellular concentration of miR-127.

In a second aspect of the present invention, the invention provides methods for the effective prophylactical or therapeutical treatment of the tubulointerstitial fibrosis or renal fibrosis associated to CKD including administering in the kidney, particularly into the resident renal cells, of a subject in need of treatment a composition comprising miR-127, a plasmid or vector comprising or consisting of a sequence coding for miR-127, a precursor of miR127 or a plasmid or vector comprising a sequence coding for a precursor of miR-127 (pre-miR-127), or a miR-127 modulator capable of increasing the intracellular concentration of miR-127, at an effective dose and an administration interval such that the fibrosis is reduced in intensity, severity, or frequency or has delayed in onset.

In a preferred embodiment of the second aspect of the invention, the resident renal cells are selected from the list consisting of Proximal tubular epithelial cells, fibroblast's renal cells and macrophages present in the kidneys. In another preferred embodiment, the resident renal cells are Proximal tubular epithelial cells and the composition comprises a miR-127, a plasmid or vector comprising a sequence coding for miR-127, a precursor of miR127 or a plasmid or vector comprising a sequence coding for a precursor of miR-127 (pre-miR-127), or a miR-127 modulator capable of increasing the intracellular concentration of miR-127. In another preferred embodiment, the resident renal cells are fibroblast's renal cells and composition comprises a miR-127, a plasmid or vector comprising a sequence coding for miR-127, a precursor of miR127 or a plasmid or vector comprising a sequence coding for a precursor of miR-127 (pre-miR-127), or a miR-127 modulator capable of increasing the intracellular concentration of miR-127. In another preferred embodiment, the resident renal cells are macrophages present in the kidneys and the composition comprises a miR-127, a plasmid or vector comprising a sequence coding for miR-127, a precursor of miR127 or a plasmid or vector comprising a sequence coding for a precursor of miR-127 (pre-miR-127), or a miR-127 modulator capable of increasing the intracellular concentration of miR-127.

In a third aspect of the present invention, the invention provides methods for the effective prophylactical or therapeutical treatment of renal fibrosis including administering in the kidney, particularly into the resident renal cells, of a subject in need of treatment a composition comprising miR-127, a plasmid or vector comprising or consisting of a sequence coding for miR-127, a precursor of miR127 or a plasmid or vector comprising a sequence coding for a precursor of miR-127 (pre-miR-127), or a miR-127 modulator capable of increasing the intracellular concentration of miR-127, at an effective dose and an administration interval such that the fibrosis is reduced in intensity, severity, or frequency or has delayed in onset.

In a preferred embodiment of the third aspect of the invention, the resident renal cells are selected from the list consisting of Proximal tubular epithelial cells, fibroblast's renal cells and macrophages present in the kidneys. In another preferred embodiment, the resident renal cells are Proximal tubular epithelial cells and the composition comprises a miR-127, a plasmid or vector comprising a sequence coding for miR-127, a precursor of miR127 or a plasmid or vector comprising a sequence coding for a precursor of miR-127 (pre-miR-127), or a miR-127 modulator capable of increasing the intracellular concentration of miR-127. In another preferred embodiment, the resident renal cells are fibroblast's renal cells and composition comprises a miR-127, a plasmid or vector comprising a sequence coding for miR-127, a precursor of miR127 or a plasmid or vector comprising a sequence coding for a precursor of miR-127 (pre-miR-127), or a miR-127 modulator capable of increasing the intracellular concentration of miR-127. In another preferred embodiment, the resident renal cells are macrophages present in the kidneys and the composition comprises a miR-127, a plasmid or vector comprising a sequence coding for miR-127, a precursor of miR127 or a plasmid or vector comprising a sequence coding for a precursor of miR-127 (pre-miR-127), or a miR-127 modulator capable of increasing the intracellular concentration of miR-127.

In a fourth aspect of the present invention, the invention provides methods for the effective prophylactical or therapeutical treatment of CKD including administering in the kidney, particularly into the resident renal cells, of a subject in need of treatment a composition comprising an anti-miR-127 or a miR-127 modulator capable of reducing the intracellular concentration of miR-127, at an effective dose and an administration interval such that at least one symptom or feature of CKD is reduced in intensity, severity, or frequency or has delayed in onset.

In a preferred embodiment of the fourth aspect of the invention, the resident renal cells are selected from the list consisting of Proximal tubular epithelial cells, fibroblast's renal cells and macrophages present in the kidneys.

In a fifth aspect of the present invention, the invention provides methods for the effective prophylactical or therapeutical treatment of the tubulointerstitial fibrosis or renal fibrosis associated to CKD including administering in the kidney, particularly into the resident renal cells, of a subject in need of treatment a composition comprising an anti-miR-127 or a miR-127 modulator capable of reducing the intracellular concentration of miR-127, at an effective dose and an administration interval such that the fibrosis is reduced in intensity, severity, or frequency or has delayed in onset.

In a preferred embodiment of the fifth aspect of the invention, the resident renal cells are selected from the list consisting of Proximal tubular epithelial cells, fibroblast's renal cells and macrophages present in the kidneys.

In a sixth aspect of the present invention, the invention provides methods for the effective prophylactical or therapeutical treatment of renal fibrosis including administering in the kidney, particularly into the resident renal cells, of a subject in need of treatment a composition comprising an anti-miR-127 or a miR-127 modulator capable of reducing the intracellular concentration of miR-127, at an effective dose and an administration interval such that the fibrosis is reduced in intensity, severity, or frequency or has delayed in onset.

In a preferred embodiment of the sixth aspect of the invention, the resident renal cells are selected from the list consisting of Proximal tubular epithelial cells, fibroblast's renal cells and macrophages present in the kidneys.

The terms "modulate," "modulation," "modify," "modulator," "modifier" and the like refer to the ability of a compound to increase or decrease the activity and/or expression of miR-127, where such function may include transcription regulatory activity and/or nucleic acid-binding. Modulation may occur in vitro or in vivo. Modulation, as described herein, includes the inhibition, antagonism, partial antagonism, activation, agonism or partial agonism of a function or characteristic associated with miR-127, either directly or indirectly, and/or the upregulation or downregulation of the expression of miR-127, either directly or indirectly. In some cases, the modulation is direct. Inhibitors or antagonists are compounds that, e.g., bind to, partially or totally block, decrease, prevent, inhibit, delay activation, inactivate, desensitize, or downregulate miR-127 activity or expression. Activators or agonists are compounds that, e.g., bind to, stimulate, increase, activate, facilitate, enhance activation, sensitize or upregulate miR-127 activity or expression. The ability of a compound to modulate the function of miR-127 can be demonstrated in a biochemical assay, e.g., in a reporter gene assay.

The "subject" is defined herein to include animals such as mammals, including, but not limited to, primates (e.g., humans), cows, sheep, goats, horses, dogs, cats, rabbits, rats, mice and the like. In some embodiments, the subject is a human.

The terms "treat," "treating," "treatment" and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention are applied preventively, prophylactically, palliatively or remedially.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

It is important to note that according to the present invention, miR-127, a pre-miR-127 or a miR-127 modulator as described herein may be delivered to the kidney, particularly into the resident renal cells, of a subject in need thereof as naked RNA (unpackaged), in the case of miR-127 or pre-miR-127, or via delivery vehicles. As used herein, the terms "delivery vehicle," "transfer vehicle," "Nanoparticle" or grammatical equivalent, are used interchangeably.

It is noted that in the examples and figures shown in the specification, "pre-miR-127" is understood as:
miRBase ID
hsa-miR-127-3p
miRBase Accession #MIMAT0000446
Product Type: mirVana® miRNA mimic
miRNA mimic for miR-127-3p (Small, synthetic, double-stranded RNA molecules designed to mimic endogenous mature miRNAs)

```
       FIRST STRAND (SAME AS miR-127)
                                    (SEQ ID NO: 1)
       5' UCGGAUCCGUCUGAGCUUGGCU 3'

(SEQ ID NO: 2)
       3' AGCCUAGGCAGACUCGAACCGA 5'
```

It is further noted that in the examples and figures shown in the specification, "anti-miR-127" is understood as:
MH10400
miRBase ID
hsa-miR-127-3p
miRBase Accession #MIMAT0000446
Product Type
mirVana® miRNA inhibitor
mirVana™ miRNA inhibitor for miR-127-3p (Small, synthetic, single-stranded RNA molecules designed to specifically bind to and inhibit mature miRNAs from functioning)

```
                                    (SEQ ID NO: 2)
       5' AGCCAAGCUCAGACGGAUCCGA 3'
```

From hereinafter we shall refer to the combination of terms miR-127, a pre-miR-127 and miR-127 modulators as "miR-127 agents".

In some embodiments, miR-127 agents may be delivered via a single delivery vehicle. In some embodiments, miR-127 agents may be delivered via one or more delivery vehicles each of a different composition. Viral carriers such as lentiviruses, adenoviruses and adeno-associated viruses; and nonviral carriers such as cationic or neutral liposomes, polyethyleneimines and atelocollagen; and single chain or peptide-targeted nanoparticles, are suitable delivery vehicles according to the present invention. In particular, according to various embodiments, suitable delivery vehicles include, but are not limited to viral vectors such as, but not limited to, lentivirus, adenoviruses or adenoassociated viruses, polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags. In particular, according to various embodiments, suitable viral vectors may carry promotors or transcription enhancers able to express miR127 specifically in resident renal cells.

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphophilic polymers and surfactants (e.g., polymerosomes, niosomes, etc.). In the context of the present invention, a liposomal delivery vehicle typically serves to transport miR-127 to a target renal cell. The process of incorporation of miR-127 into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the miR-127 agents contained therein and/or facilitate the delivery of miR-127 agents to the target renal cell.

In some embodiments, liposomes may comprise one or more cationic lipids. As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, CI 2-200 described at paragraph [00225]) and WO 2012/170930, both of which are incorporated herein by reference.

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the lipid nanoparticle may be greater than 5, %, 10%, greater than 20%, greater than 30%, or greater than 40%.

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 5 kDa in length covalently attached to a lipid with alkyl chain(s) of $C_6$-$C_2$0 length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDA, e.g., 25 kDa branched PEI (Sigma #408727).

In certain embodiments of the invention, the provided compositions can be administered prior to or subsequent to the appearance of disease symptoms (renal fibrosis). In certain embodiments, the provided composition is administered to patients with familial histories of the disease, or who have phenotypes that may indicate a predisposition to the disease, or who have been diagnosed as having a genotype which predisposes the patient to the disease, or who have other risk factors.

As already stated in any of the first to third aspects above, the provided compositions are administered to the subject in a therapeutically effective amount.

Synthesis of miR-127 miR-127 according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of miRNA according to the invention, a DNA template is transcribed in vitro. A suitable DNA template typically has a promoter, for example a T3, T7 or SP6 promoter, for transcription, followed by desired nucleotide sequence for desired mRNA and a termination signal.

Modified miR-127

In some embodiments, miR-127 according to the present invention may be synthesized as unmodified or modified miRNA. Typically, mRNAs are modified to enhance stability. Modifications of miR-127 can include, for example, modifications of the nucleotides of the RNA. A modified miR-127 according to the invention can thus include, for example, backbone modifications, sugar modifications or base modifications. In some embodiments, miR-127s may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, miR-127s may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, miR-127s may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, miR-127s may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate.

Typically, miR-127 synthesis may include the addition of a "cap" on the N-terminal (5') end, and a "tail" on the C-terminal (3') end. The presence of the cap provides resistance to nucleases found in most eukaryotic cells. The presence of a "tail" serves to protect the mRNA from exonuclease degradation.

Thus, in some embodiments, miR-127s include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

In some embodiments, miR-127s include a 3' poly(A) tail structure. A poly-A tail on the 3' terminus of mRNA typically includes about 10 to 300 adenosine nucleotides (SEQ ID NO:9) (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (SEQ ID NO:10) (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, miR-127 includes a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Pharmaceutical Compositions

As already stated above, the present invention thus provides, among other things, methods and compositions for the effective prophylactical or therapeutical treatment of CKD, particularly for the prophylactical or therapeutical treatment of the tubulointerstitial fibrosis associated to CKD, more particularly for the prophylactical or therapeutical treatment of renal fibrosis.

To facilitate expression of miR-127 agents in vivo, any of the delivery vehicles above mentioned, such as liposomes or viral carriers, can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated or associated miR-127 agents and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art.

Suitable routes of administration include, for example, oral, rectal, vaginal, transmucosal, or intestinal administration; parenteral delivery, including intradermal, transdermal (topical), intramuscular, subcutaneous, intramedullary injections, as well as intrathecal, direct intraventricular, intravenous, intraperitoneal, or intranasal.

Alternately or additionally, liposomally encapsulated miR-127 agents and compositions of the invention may be administered in a local rather than systemic manner, for example, via injection of the pharmaceutical composition directly into the targeted renal tissue, preferably in a sustained release formulation.

Provided methods of the present invention contemplate single as well as multiple administrations of a therapeutically effective amount of the miR-127 agents. In some embodiments, provided liposomes and/or compositions are formulated such that they are suitable for extended-release of the miR-127 agents contained therein. Such extended-release compositions may be conveniently administered to a subject at extended dosing intervals. For example, in one embodiment, the compositions of the present invention are administered to a subject twice day, daily or every other day. In a preferred embodiment, the compositions of the present invention are administered to a subject twice a week, once a week, every 7 days, every 10 days, every 14 days, every 28 days, every 30 days, every two weeks (e.g., every other week), every three weeks, or more preferably every four weeks, once a month, every six weeks, every eight weeks, every other month, every three months, every four months, every six months, every eight months, every nine months or annually. Also contemplated are compositions and liposomes which are formulated for depot administration (e.g., intramuscularly, subcutaneously) to either deliver or release a mRNA over extended periods of time. Preferably, the extended-release means employed are combined with modifications made to the mRNA to enhance stability As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating renal fibrosis). For example, a therapeutically effective amount may be an amount sufficient to achieve a desired therapeutic and/or prophylactic effect. Generally, the amount of the miR-127 agents administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

According to the present invention, a therapeutically effective dose of the provided composition, when administered regularly, results in reduced expression of renal fibrosis as compared to levels before treatment.

In some embodiments, administering provided compositions results in reduced renal fibrosis by at least about 10%, 20%, 30%, 40%, 50%, 60%, 70%, 80%, 90%, or 95% as compared to fibrotic levels before treatment.

In some embodiments, the therapeutically effective dose ranges from about 0.005 to 500 mg/kg body weight, e.g., from about 0.005 to 400 mg/kg body weight, from about 0.005 to 300 mg/kg body weight, from about 0.005 to 200 mg/kg body weight, from about 0.005 to 100 mg/kg body weight, from about 0.005 to 90 mg/kg body weight, from about 0.005 to 80 mg/kg body weight, from about 0.005 to 70 mg/kg body weight, from about 0.005 to 60 mg/kg body weight, from about 0.005 to 50 mg/kg body weight, from about 0.005 to 40 mg/kg body weight, from about 0.005 to 30 mg/kg body weight, from about 0.005 to 25 mg/kg body weight, from about 0.005 to 20 mg/kg body weight, from about 0.005 to 15 mg/kg body weight, from about 0.005 to 10 mg/kg body weight. In some embodiments, the mRNA is administered at a dose ranging from about 0.1-5.0 mg/kg body weight, for example about 0.1-4.5, 0.1-4.0, 0.1-3.5, 0.1-3.0, 0.1-2.5, 0.1-2.0, 0.1-1.5, 0.1-1.0, 0.1-0.5, 0.1-0.3, 0.3-5.0, 0.3-4.5, 0.3-4.0, 0.3-3.5, 0.3-3.0, 0.3-2.5, 0.3-2.0, 0.3-1.5, 0.3-1.0, 0.3-0.5, 0.5-5.0, 0.5-4.5, 0.5-4.0, 0.5-3.5, 0.5-3.0, 0.5-2.5, 0.5-2.0, 0.5-1.5, or 0.5-1.0 mg/kg body weight.

In some embodiments, the therapeutically effective dose is or greater than about 0.1 mg/kg body weight, about 0.5 mg/kg body weight, about 1.0 mg/kg body weight, about 3 mg/kg body weight, about 5 mg/kg body weight, about 10 mg/kg body weight, about 15 mg/kg body weight, about 20 mg/kg body weight, about 30 mg/kg body weight, about 40 mg/kg body weight, about 50 mg/kg body weight, about 60 mg/kg body weight, about 70 mg/kg body weight, about 80 mg/kg body weight, about 90 mg/kg body weight, about 100 mg/kg body weight, about 150 mg/kg body weight, about 200 mg/kg body weight, about 250 mg/kg body weight, about 300 mg/kg body weight, about 350 mg/kg body weight, about 400 mg/kg body weight, about 450 mg/kg body weight, or about 500 mg/kg body weight. In some embodiments, the therapeutically effective dose is administered at a dose of or less than about 5.0, 4.5, 4.0, 3.5, 3.0, 2.5, 2.0, 1.5, 1.0, 0.8, 0.6, 0.5, 0.4, 0.3, 0.2, or 0.1 mg/kg body weight.

Also contemplated herein are lyophilized pharmaceutical compositions comprising one or more of the liposomes disclosed herein and related methods for the use of such compositions as disclosed for example, in U.S. Provisional Application No. 61/494,882, filed Jun. 8, 2011, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

EXAMPLES

Materials and Methods

Overexpression and inhibition of miR127-3p was performed by transient transfection of mature miR-127-3p and anti-miR127-3p, using Lipofectamine 2000.

Expression of EMT and miR127 has been determined by qRT-PCR using specific primers and SYBRGreen, in total RNA extracted from cell lysates (see figures)

Activity of metalloproteinases (MMPs) has been estimated using zimograms, where MMP activity, if present, is able to digest gelatin added to acrylamide matrix (see figures)

Wound-healing assay is an in vivo assay where a wound in the cell monolayer is made using a pipet type and healing of the wound is observed by microscopy (see figures)

Expression of miR127 has been determined by qRT-PCR using specific primers and SYBRGreen, in total RNA extracted from total renal lysates (see figures)

In situ hybridization for miR-127-3p localization in renal tissue was performed on paraffin-embedded renal tissue using specific double DIG (digoxigenine) labeled probe for miR-127 (see figures).

Expression of miR127 has been determined by qRT-PCR using specific primers and SYBRGreen, in total RNA extracted from total renal lysate of human biopsy (see figures)

Example 1. Inhibition of Proliferation and Transformation of Resident Renal Fibroblasts In cultures of normal rat fibroblasts NRK49F unstimulated with TGF-β the single overexpression of miR-127 inhibited their proliferation and the culture of NRK49F fibroblasts in supernatants obtained from HK-2 cells in which miR-127 was overexpressed, resulted in the apoptosis of the NRK49F fibroblasts.

This example illustrates that expression of miR-127 results in the inhibition of proliferation and transformation of resident renal fibroblasts to myofibroblasts, which secrete abnormal extracellular matrix proteins such as collagen I, which is deposited and contributes crucially to fibrosis.

Example 2. miR-127 is Expressed in Human Biopsies of Patients Suffering from CKD qRT-PCR of miR-127 in human biopsies of patients suffering from CKD (Grade I, Grade II and Grade III according to the classification of Banff) indicates that the expression of miR-127 increases with the severity of the damage; furthermore, in situ hybridization of miR-127 in these biopsies can locate miR-127 in proximal tubules exhibiting tubular atrophy.

In addition, miR-127 is secreted by tubular cells as shown by tests performed in supernatants of tubular cells and serum of patients with CKD in varying degrees, by qRT-PCR, in which miR-127 is no longer detected in the serum of those patients suffering from the final stages of CKD (stage III advanced, stage IV and stage V).

Example 3. miR-127 Expression Induces the M1 Phenotype in Human Macrophages

Supernatants obtained from human proximal tubular cells (HK2) modulated with miR-127 (overexpressed or inhibited), were added to human primary macrophages promoting a change in their polarization. In this sense, supernatants from HK2 tubular cells overexpressing miR-127 promoted the M1 phenotype. In contrast, supernatants from HK2 tubular cells in which miR-127 was inhibited promoted the M2 phenotype.

In view of the above, we characterized the above mentioned supernatants. In this sense, the supernatants obtained from HK-2 tubular cells overexpressing miR-127 presented cytokines priming the M1 phenotype. In contrast, supernatants obtained from HK2 tubular cells in which miR-127 expression was inhibited, presented cytokines priming the M2 phenotype. Moreover, the induction of the M1 phenotype by addition of GMCSF+LPS to the culture medium of primary human macrophages, resulted in the upregulation of miR-127 in the human macrophages and the induction of the M2 phenotype. Furthermore, the addition of GMCSF+IL4 or GMCSF+IL10 to the culture medium of primary human macrophages, resulted in the inhibition of miR-127 expression in the human macrophages.

The results indicated in examples 1 and 3 and illustrated in the figures, clearly suggest that miR-127 is a key factor in chronic kidney damage, with an important role in the EMT of tubular cells and a regulatory role of in the fibrotic microenvironment, modulating the proliferation of fibroblasts and the polarization of macrophages in renal parenchyma.

Lastly, it is noted that we have collaborated with Dr Lama's group in the recent paper (Fierro et al., *EMBO Rep.* 2015 October; 16(10):1358-77. doi: 10.15252/embr.201540750. Epub 2015 Aug. 27. miR-9-5p suppresses pro-fibrogenic transformation of fibroblasts and prevents organ fibrosis by targeting NOX4 and TGFBR2), identifying miR-9-5p as a critical mediator of pulmonary fibrosis. Preliminary results in RNA from paraffin-embedded sections of lung biopsies of idiopathic fibrotic patients indicates that miR-127 exhibited different regulation of miR-9. Moreover, qRT-PCR of miR-9-5p in RNA from UUO models indicate also a different modulation (downregulation) of this miR-9 in these model of renal fibrosis. These results indicate that different miRNAs are differentially expressed in different pathological contexts, pointing out that miR-127-3p is important for renal fibrosis in comparison with fibrosis in other solid organs

The invention claimed is:

1. A method for prophylactic or therapeutic treatment of renal fibrosis in a subject in need thereof, comprising administering an effective dose of a composition comprising a miR-127, a plasmid or vector comprising a sequence coding for miR-127, a precursor of miR127 or a plasmid or vector comprising a sequence coding for a precursor of miR-127, in the kidney of the subject.

2. The method of claim 1, wherein said composition comprises a delivery vehicle of miR-127.

3. The method of claim 2, wherein the delivery vehicle is selected from the group consisting of viral vectors, lentiviruses, adenoviruses, adenoassociated viruses, polymer based carriers, polyethyleneimine (PEI), lipid nanoparticles, liposomes, nanoliposomes, ceramide-containing nanoliposomes, proteoliposomes, natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers, dry powder formulations, plasmids, viruses, calcium phosphate nucleotides, aptamers, peptides and vectorial tags.

4. The method of claim 3, wherein the delivery vehicle is a viral vector selected from the group consisting of lentiviruses, adenoviruses and adenoassociated viruses.

5. The method of claim 3, wherein the delivery, vehicle is a liposome.

6. The method of claim 1, wherein said composition is administered by a route selected from the group consisting of oral, rectal, vaginal, transmucosal, intestinal, parenteral, intradermal, transdermal, intramuscular, subcutaneous, intramedullary injections, intrathecal injection, direct intraventricular, intravenous, intraperitoneal, and intranasal.

7. The method of claim 1, wherein said composition is administered by local manner, via injection of the composition directly into a targeted renal tissue, wherein the composition is formulated in a sustained release formulation.

8. The method of claim 4, comprising administering the composition into resident renal cells of the subject.

9. The method of claim 3, wherein the multi-domain-block polymers are selected from the group consisting of vinyl polymers, polypropyl acrylic acid polymers and dynamic polyconjugates.

* * * * *